US005846706A

United States Patent [19]
Greenberg et al.

[11] Patent Number: 5,846,706
[45] Date of Patent: Dec. 8, 1998

[54] RAPID AND SENSITIVE DETECTION OF HERPES SIMPLEX VIRUS

[75] Inventors: Steven J. Greenberg, Orchard Park; Mary Jo Evans, East Amherst, both of N.Y.

[73] Assignee: Health Research Inc., Buffalo, N.Y.

[21] Appl. No.: 600,764

[22] Filed: Feb. 13, 1996

Related U.S. Application Data

[62] Division of Ser. No. 428,370, Apr. 25, 1995, Pat. No. 5,569,583.

[51] Int. Cl.[6] .............................. C12Q 1/68; C12P 19/34; C07H 21/04
[52] U.S. Cl. ................................ 435/5; 435/6; 435/912; 435/810; 536/24.32; 536/24.33; 935/8; 935/11; 935/78
[58] Field of Search ..................................... 435/6.5, 91.2, 435/810; 536/24.32, 24.33; 935/77, 78, 8, 11

[56] References Cited

U.S. PATENT DOCUMENTS 5,514,577  5/1996  Draper ..................................... 435/238

FOREIGN PATENT DOCUMENTS 9419945  9/1994  WIPO .

OTHER PUBLICATIONS

Shimizu et al. Molecular and Cellular Probes (1994) 8:193–198.

*Primary Examiner*—Carla J. Myers
*Attorney, Agent, or Firm*—Hodgson, Russ, Andrews, Woods & Goodyear

[57] ABSTRACT

The present invention relates to novel compositions comprising herpesvirus-specific oligonucleotides which are useful as primers to amplify particular regions of the genome either herpes simplex virus or cytomegalovirus during enzymatic nucleic acid amplification. The invention also provides a rapid, sensitive and specific method for the detection of the respective herpesvirus which may be present in a clinical specimen, using the herpesvirus-specific primers and enzymatic nucleic acid amplification; hybridization of amplified target sequences, if present, with one or more herpesvirus-specific oligonucleotide probes which are labeled with a detectable moiety; and detection of the detectable moiety of labeled oligonucleotide probe hybridized to amplified target sequences of herpesvirus DNA.

8 Claims, 5 Drawing Sheets

RAPID AND SENSITIVE DETECTION OF HERPES SIMPLEX VIRUS

This is divisional of application Ser. No. 0/8,428,370 filed on Apr. 25, 1995, now U.S. Pat. No. 5,569,583.

1. FIELD OF THE INVENTION

The present invention relates to novel compositions and methods for detecting the presence of herpesviruses that frequently infect humans and are associated with the development of human disease. More particularly, the invention is directed to an accurate and sensitive method for the diagnosis of herpesvirus infection using specific oligonucleotides as primers to amplify particular regions of the genome of the agent of herpesvirus sought to be detected in a clinical specimen. Herpesvirus-specific oligonucleotides may be used in the subsequent detection of the amplified regions of DNA.

2. BACKGROUND OF THE INVENTION

Herpesviruses are a group of ubiquitous viruses which bear both structural and compositional resemblance. Most agents of the herpesvirus group can integrate their DNA into that of the host cell (particularly lymphoid cells or ganglia) after infecting the human host, thereby causing a latent infection which has the potential to reactivate and cause recurrent disease. There are at least six herpesviruses which are known to frequently infect humans, including herpes simplex virus type 1 (HSV-1), herpes simplex virus type 2 (HSV-2), cytomegalovirus (CMV), Epstein-Barr virus (EBV), varicella-zoster virus (VZV), and Human herpesvirus 6 (HHV-6).

2.1 Herpes Simplex Virus Infection

Herpes simplex virus (HSV) causes, or is associated with, a wide variety of diseases in humans (Table 1).

TABLE 1

Diseases caused by Herpes Simplex Virus

| | |
|---|---|
| genital lesions | stomatitis |
| encephalitis | herpetic dermatitis |
| meningitis | pharyngitis |
| keratoconjunctivitis | pneumonia |
| neonatal herpes | keratitis |
| chorioretinitis | herpetic hepatitis |
| eczema herpeticum | erythema multiforme |

There are instances in which rapid, sensitive, and specific diagnosis of HSV disease is imperative. The most serious HSV infection is encephalitis. Encephalitis is often a disseminated infection in newborns which may be acquired either during or after birth; and an adult infection affecting the temporal lobe of the brain. Currently, definitive diagnosis is by brian biopsy and culture to isolate HSV. Serologic diagnosis, particularly of HSV in cerebrospinal fluid (CSF), is not sufficiently sensitive or specific, and takes too much time to be of use in decisions involving choices for early therapeutic intervention of encephalitis. Early therapy of patients with encephalitis, before irreversible hemorrhagic necrosis of the brain, has resulted in improved outcomes.

Further, due to the high morbidity and mortality of infants having neonatal herpes infection, and since many cases of neonatal HSV infection can be prevented by cesarean section, diagnosis of maternal infection before delivery is important. Since cultures of the mother taken days or weeks before delivery do not predict well whether the mother may be symptomatic at the time of delivery, a rapid, sensitive, and specific assay for detecting HSV in body fluids or secretions is desirable as a means to monitor infection, and consequently, determine the necessity of cesarean section.

Additionally, there are instances in which knowing the infecting serotype is helpful; i.e. whether infection is cause by HSV-1 or HSV-2. Since both HSV-1 and HSV-2 share antigens, serological differentiation is difficult. Distinguishing between infection caused by HSV-1 and HSV-2 may be important because it has been reported that sensitivity to antiviral therapy can vary with the serotype. Identifying the serotype can also provide prognostic information. For example, genital infections caused by HSV-1 are less likely to recur than those infections caused by HSV-2.

2.2 Diagnosis of HSV Infection

Current methods for the detection of HSV in clinical specimens have been routinely accomplished by using the clinical specimens to infect susceptible cell lines in amplifying the amount of virus (antigen) to increase the sensitivity and specificity of detection; isolating the virus from the cultured cell lines; and subsequently immunologically confirming the virus identity. The disadvantages of such methods of detection include that the time required for complete diagnosis can range from 1–12 days, depending on the sensitivity of the cells inoculated and the amount of virus in the inoculum; and that the methods are both labor and time intensive, and expensive.

Immunological assays, including immunofluorescence (IF) or enzyme-linked immunosorbent assays (ELISA) or radioimmunoassays (RIA) usually have good sensitivity. However, such immunoassays can suffer from either lack of good specificity or sensitivity, and lack of good reproducibility. For example, certain clinical specimens, such as vesicle fluid and mucus or other body secretions, can bind nonspecifically to proteins such as antibodies or antigen. Sensitivity depends on the titer of antibody found in the clinical specimen, which in the case of herpes simplex encephalitis, occurs in the CSF weeks after infection. Additionally, early therapeutic intervention (e.g., with acyclovir) can attenuate antibody response after some primary infections (Kahlon et al., 1987, *J. Infect. Dis.* 155:38–43). Reproducibility can vary with the lot of antisera used and/or the lot of microtitration plates, which may vary in their binding abilities.

Recent advances in molecular biology have spurred the use of DNA probes in attempts to provide a more rapid, sensitive and specific assay for detecting HSV in clinical specimens. For example, a radiolabeled DNA probe has been used to hybridize to tissue cultures infected with or by HSV, or in clinical samples suspected of containing HSV ("hybridization assays"). However, probing of tissue cultures requires at least 18–24 hours for growth to amplify the antigen (HSV) to be detected, if present, and further time for development of autoradiographic detection systems. Using hybridization assays for assaying clinical specimens for HSV may lack sensitivity, depending upon the titer of virus and the clinical sample assayed. Detection of HSV in clinical samples has been reported using the polymerase chain reaction (PCR) to enzymatically amplify HSV DNA (Cao et al., 1989, *J. Invest. Dermatol.* 92:391–392; Powell et al., 1990, *Lancet,* 335:357–358; Rowley et al., 1990, *Lancet,* 335:440–441; and Aurelius et al., 1991, *Lancet,* 337:189–192). However, because of the dangers of false positive reactions, these procedures require rigid controls to prevent contamination and carry over (Ehrlich et al., 1994, pp.3–18 in *PCR-Based Diagnostics in Infectious Diseases,* G D Ehrlich and S J Greenberg (eds), Blackwell Scientific Publications). Therefore, there exists a need for a rapid, sensitive, and specific assay for herpesvirus, HSV-1 and HSV-2.

2.3 Cytomegalovirus Infection

Cytomegalovirus (CMV) causes, or is associated with, a wide variety of diseases in humans (Table 2). More than 90% of bone marrow or kidney transplant recipients (immunocompromised hosts) develop CMV infections, most of which are due to reactivation of latent virus by immunosuppressive drugs, as well as transmission of virus by latently infected donor tissue or blood (Ackerman et al., 1988, *Transplant. Proc.* 20(S1):468–71; Peterson et al., 1980, *Medicine* 59:283–300).

TABLE 2

Diseases caused by Cytomegalovirus

| | |
|---|---|
| cytomegalic inclusion disease in neonates | heterophil-negative mononucleosis |
| interstitial pneumonia | pneumonitis |
| retinitis | hepatitis |
| pancreatitis | meningoencephalitis |
| gastrointestinal disease | disseminated infection |

2.4 Diagnosis of CMV Infection

There are instances in which rapid, sensitive, and specific diagnosis of CMV disease is imperative. In recent years, the number of patients undergoing organ and tissue transplantations has increased markedly. CMV is the most frequent cause of death in immunocompromised transplant recipients, thereby confirming the need for rapid and reliable laboratory diagnosis. Lymphocytes, monocytes, and possibly arterial endothelial or smooth muscle cells, are sites of CMV latency. Therefore, prevention of CMV infections in immunocompromised individuals (e.g., transplant recipients) includes use of CMV-negative blood products and organs. Additionally, CMV can be spread transplacentally, and to newborns by contact with infected cervical secretions during birth. Thus, a rapid, sensitive, and specific assay for detecting CMV in body fluids or secretions may be desirable as a means to monitor infection, and consequently, determine the necessity of cesarean section.

Diagnosis of CMV infection may be performed by conventional cell culture using human fibroblasts; shell vial centrifugation culture utilizing monoclonal antibodies and immunofluorescent staining techniques; serological methods; the CMV antigenemia assay which employs a monoclonal antibody to detect CMV antigen in peripheral blood leukocytes (PBLs); or by nucleic acid hybridization assays. These various methods have their advantages and limitations. Conventional cell culture is sensitive but slow, as cytopathic effect (CPE) may take 30 or more days to develop. Shell vial centrifugation is more rapid but still requires 24–48 hours for initial results. Both culture methods are affected by antiviral therapy. In immunocompromised patients, the ability to mount IgG and/or IgM antibody responses to CMV infection are impaired, and serological methods are thus not reliable in this setting. Alternatively, IgM antibodies may be persistent for months after infection is resolved, and thus their presence may not be indicative of active infection. The CMV antigenemia assay is labor intensive and is not applicable to specimens other than PBLs.

Recent advances in molecular biology have spurred the use of DNA probes in attempts to provide a more rapid, sensitive and specific assay for detecting CMV in clinical specimens. For example, radiolabeled DNA probes have been used to hybridize to tissue cultures infected with or by CMV, or in clinical samples suspected of containing CMV ("hybridization assays"). However, probing of tissue cultures requires at least 18–24 hours for growth to amplify the antigen (CMV) to be detected, if present, and additional time for development of autoradiographic detection systems. Using hybridization assays for assaying clinical specimens for CMV may lack sensitivity, depending upon the titer of virus and the clinical sample assayed. Detection of CMV in clinical samples has been reported using the polymerase chain reaction (PCR) to enzymatically amplify CMV DNA. Methods using PCR compare favorably with virus isolation, in situ hybridization assays, and Southern blotting (See for example, Bamborschke et al., 1992, *J. Neurol.* 239:205–208; Drouet et al., 1993, *J. Virol. Methods* 45:259–276; Einsele et al., 1991, *Blood* 77:1104–1110; Einsele et al., 1991, *Lancet* 338:1170–1172; Lee et al., 1992, *Aust. NZ J. Med.* 22:249–255; Miller et al., 1994, *J. Clin. Microbiol.* 32:5–10; Rowley et al., 1991, *Transplant.* 51:1028–1033; Spector et al., 1992, *J. Clin. Microbiol.* 30:2359–2365; and Stanier et al., 1992, *Molec. Cell. Probes* 8:51–58). Others, comparing the CMV antigenemia assay with PCR methods, have found PCR methods as efficient or slightly more efficient in the detection of CMV (van Dorp et al., 1992, *Transplant.* 54:661–664; Gerna et al., 1991, *J. Infect. Dis.* 164:488–498; Vleiger et al., 1992, *Bone Marrow Transplant.* 9:247–253; Zipeto et al., 1992, *J. Clin. Microbiol.* 30:527–530). In addition, PCR methods have exhibited great sensitivity when specimens other than PBLs are assayed (Natori et al., 1993, *Kansenshogaku Zasshi* 67:1011–1015; Peterson et al., 1980, *Medicine,* 59:283–300; Prosch et al., 1992, *J. Med. Virol.* 38:246–251; Ratnamohan et al., 1992, *J. Med. Virol.* 38:252–259). However, because of the dangers of false positive reactions, these procedures require rigid controls to prevent contamination and carry over (Ehrlich et al., 1994, pp.3–18 in *PCR-Based Diagnostics in Infectious Diseases,* G D Ehrlich and S J Greenberg (eds), Blackwell Scientific Publications). Therefore, there exists a need for a rapid, sensitive, and specific assay for herpesvirus, CMV.

3. SUMMARY AND OBJECTS OF THE INVENTION

The present invention is directed to nucleic acid sequences (oligonucleotides) useful as primers and/or probes in the detection of a herpesvirus in clinical specimens. Also, the present invention is directed to a method of detecting the presence of herpesvirus in a clinical specimen wherein the oligonucleotides of the present invention may be used to amplify target nucleic acid sequences of a herpesvirus that may be contained within a clinical specimen, and/or to detect the presence or absence of amplified target nucleic acid sequences of the herpesvirus. Respective oligonucleotides may be used to amplify and/or detect HSV and CMV nucleic acid sequences. By using the oligonucleotides of the present invention and according to the methods of the present invention, as few as one to ten copies of the herpesvirus genome may be detected in the presence of milligram quantities of extraneous DNA.

One object of the present invention is to provide oligonucleotides which can be used as primers to amplify specific nucleic acid sequences of HSV.

Another object of the present invention is to provide oligonucleotides which can be used as probes in the detection of amplified specific nucleic acid sequences of HSV.

Another object of the present invention is to provide oligonucleotides which can be used as probes in the detection of amplified specific HSV nucleic acid sequences, and which distinguish serotypes of HSV; i.e., HSV-1 from HSV-2.

A further object of the present invention is to provide an accurate and sensitive method for detecting the presence of HSV that may be contained in clinical specimens by using the oligonucleotides disclosed to amplify and detect specific nucleic acid sequences of HSV.

Another object of the present invention is to provide oligonucleotides which can be used as primers to amplify specific nucleic acid sequences of CMV.

Another object of the present invention is to provide oligonucleotides which can be used as probes in the detection of amplified specific nucleic acid sequences of CMV.

A further object of the present invention is to provide an accurate and sensitive method for detecting the presence of CMV that may be contained in clinical specimens by using the oligonucleotides disclosed to amplify and detect specific nucleic acid sequences of CMV.

4. BRIEF DESCRIPTION OF THE FIGURES

In the accompanying drawings.

Figure 1A:
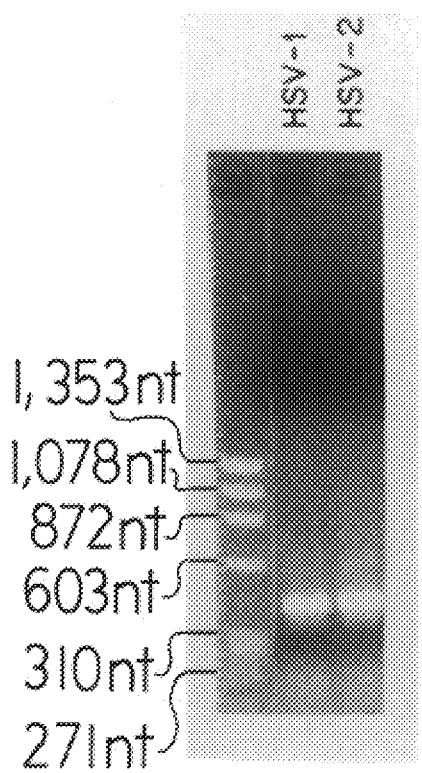
FIG. 1A represents a gel corresponding to enzymatic amplification of HSV-1 genomic DNA and HSV-2 genomic DNA using polymerase gene primers (SEQ ID NOs:7 & 8).

5. DETAILED DESCRIPTION OF THE INVENTION 5.1 Definitions

By the terms "enzymatically amplify" or "amplify" is meant, for the purposes of the specification or claims, a process by which nucleic acid sequences are amplified in number. There are several means for enzymatically amplifying nucleic acid sequences. Currently the most commonly used method, PCR (polymerase chain reaction, Cetus Corporation) involves the use of a thermostable DNA polymerase, known sequences as primers, and heating cycles which separate the replicating deoxyribonucleic acid (DNA) strands and exponentially amplify a gene of interest. Other amplification methods include LCR (ligase chain reaction, BioTechnica International) which utilizes DNA ligase, and a probe consisting of two halves of a DNA segment that is complementary to the sequence of the DNA to be amplified; enzyme QB replicase (Gene-Trak Systems) and a ribonucleic acid (RNA) sequence template attached to a probe complementary to the DNA to be copied which is used to make a DNA template for exponential production of complementary RNA; and NASBA (nucleic acid sequence-based amplification, Cangene Corporation) which can be performed on RNA or DNA as the nucleic acid sequence to be amplified.

By the term "composition" is meant, for the purposes of the specification or claims, a combination of elements which may include one or more of the following: the reaction buffer for the respective method of enzymatic amplification, plus one or more oligonucleotides specific for herpesvirus CMV or HSV-1 or HSV-2; and one or more oligonucleotides specific for herpesvirus CMV or HSV-1 or HSV-2, wherein said oligonucleotide is labeled with a detectable moiety.

By the term "complementarity" or "complementary" is meant, for the purposes of the specification or claims, a sufficient number in the oligonucleotide of complementary base pairs in its sequence to interact specifically (hybridize) with the target nucleic acid sequence of the herpesvirus to be amplified or detected. As known to those skilled in the art, a very high degree of complementarity is needed for specificity and sensitivity involving hybridization, although it need not be 100%. Thus, for example, an oligonucleotide which is identical in nucleotide sequence to an oligonucleotide disclosed herein, except for one base change or substitution, may function equivalently to the disclosed oligonucleotides.

By the terms "consisting essentially of a nucleotide sequence" is meant, for the purposes of the specification or claims, the nucleotide sequence disclosed, and also encompasses nucleotide sequences which are identical except for a one base change or substitution therein.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated when the oligonucleotide is hybridized to amplified herpesvirus sequences. Thus, "detectable moiety" is used synonymously with "label molecule". Synthesis of oligonucleotides can be accomplished by any one of several methods known to those skilled in the art. To label an oligonucleotide with a detectable moiety, detectable moiety-labeled dUTP may be added in the process of synthesizing the oligonucleotide so that the detectable moiety is incorporated directly into the oligonucleotide (See for example, *Molecular Cloning*, a laboratory manual: editors Sambrook, Fritsch, Maniatis; Cold Spring Harbor Laboratory Press, 1989; *BioTechniques* "Producing single-stranded DNA probes with the Taq DNA polymerase: a high yield protocol," 10:36, 1991). Alternatively, the detectable moiety may be incorporated "indirectly" such as, for example, by biotinylating the 5' aminogroup of the oligonucleotide with sulfo-NHS-biotin. Other label molecules, known to those skilled in the art as being useful for detection, include chemiluminescent or fluorescent molecules. Various fluorescent molecules are known in the art which are suitable for use to label a nucleic acid substrate for the method of the present invention. Fluorescent molecules used as labels may include amine-reactive molecules which are reactive to end terminal amines of the substrate; sulfonyl chlorides which are conjugated to the substrate through amine residues; and the like. Depending on the fluorescent molecule used, incorporating the substrate with the fluorescent molecule label include attachment by covalent or noncovalent means. The protocol for such incorporation may vary depending upon the fluorescent molecule used. Such protocols are known in the art for the respective fluorescent molecule.

5.2 The Method as Applied to Detection of CMV

One embodiment of the present invention is directed to CMV-specific oligonucleotides which can be used to amplify sequences of CMV DNA, and to subsequently determine if amplification has occurred, from DNA extracted from a clinical specimen. A pair of CMV-specific DNA oligonucleotide primers are used to hybridize to CMV genomic DNA that may be present in DNA extracted from a clinical specimen, and to amplify the specific segment of genomic DNA between the two flanking primers using enzymatic synthesis and temperature cycling. Each pair of primers are designed to hybridize only to the CMV DNA to which they have been synthesized to complement; one to each strand of the double-stranded DNA. Thus, the reaction is specific even in the presence of microgram quantities of heterologous DNA. For the purposes of this description, the primer derived from the sequence of the positive strand of DNA will be referred to as the "positive (+) primer", and the primer derived from the sequence of the negative strand will be referred to as the "negative (−) primer".

Amplification of DNA may be accomplished by any one of the methods commercially available. For example, the polymerase chain reaction may be used to amplify the DNA. Once the primers have hybridized to opposite strands of the target DNA, the temperature is raised to permit replication of the specific segment of DNA across the region between the two primers by a thermostable DNA polymerase. Then the reaction is thermocycled so that at each cycle the amount of DNA representing the sequences between the two primers is doubled, and specific amplification of the CMV DNA sequences, if present, results.

Further identification of the amplified DNA fragment, as being derived from CMV DNA, may be accomplished by liquid hybridization. This method utilizes one or more oligonucleotides labeled with detectable moiety as probes to specifically hybridize to the amplified segment of CMV DNA. Detection of the presence of sequence-specific amplified CMV DNA may be accomplished using a gel retardation assay with subsequent detection of the complex comprising the labeled oligonucleotide hybridized to the sequence-specific amplified CMV DNA ("amplified target sequences").

In such a enzymatic amplification reaction-liquid hybridization system of CMV detection, cells from a specimen of blood, amniotic fluid, urine, secretions, or other body fluid is subjected to a rapid DNA extraction procedure (See for example, Bamborschke et al., 1992, supra). Then, for example, the DNA extracted from the clinical specimen is enzymatically amplified in the polymerase chain reaction using CMV-specific oligonucleotides (SEQ ID NO:1 & SEQ ID NO:2; or SEQ ID NO:3 & SEQ ID NO:4) as primer pairs. Following amplification, CMV-specific oligonucleotides (SEQ ID NO:5, for use with SEQ ID NOs:1 & 2; or SEQ ID NO:6, for use with SEQ ID NOs:3 & 4) radiolabeled with $^{32}$P are hybridized to the amplified target sequences, if present.

The contents of the hybridization reaction are then analyzed by electrophoresis on a polyacrylamide gel. If the sequence-specific amplified CMV DNA is present in the DNA extracted from the clinical specimen, the migration of the labeled oligonucleotide probe through the gel will be retarded by hybridization with the sequence-specific amplified CMV DNA. Visualization of this gel retardation can be accomplished by autoradiography in 24–48 hours. Alternatively, by labelling the oligonucleotide probe with a fluorescent molecule, or by electrophoresing the amplified DNA in the presence of a fluorescent intercalating dye (e.g., Sybr Green I), the acrylamide gel can be scanned by a fluorescent imager for fluorescent DNA thereby allowing completion of the assay in approximately 6 hours.

Using the oligonucleotides and the enzymatic amplification reaction-liquid hybridization system for CMV detection according to the present invention, and using radiolabeled oligonucleotide probes, 6 to 0.6 $TCID_{50}$ (tissue culture infective dose, 50%) of CMV DNA has been detected in samples containing 10 micrograms of heterologous DNA. Using the compositions and the system for CMV detection according to the present invention, and using fluorescent imaging, 0.03 $TCID_{50}$ of CMV DNA has been detected in samples containing 10 micrograms of heterologous DNA. Thus, the oligonucleotides of the present invention have commercial applications in diagnostic kits for the detection of CMV DNA in clinical specimens.

In a related embodiment of the present invention, the CMV-specific oligonucleotides may be used to amplify and detect CMV DNA from DNA extracted from a clinical specimen. In this embodiment, the oligonucleotides used as primers may be labeled directly with detectable moiety, or synthesized to incorporate the label molecule. Depending on the label molecule used, the amplification products can then be detected, after binding onto an affinity matrix, using isotopic or calorimetric detection.

5.3 The Method as Applied to Detection of HSV

Another embodiment of the present invention is directed to HSV-specific oligonucleotides which can be used to amplify sequences of HSV DNA, and to subsequently determine if amplification has occurred, from DNA extracted from a clinical specimen. A pair of HSV-specific DNA oligonucleotide primers are used to hybridize to HSV genomic DNA that may be present in DNA extracted from a clinical specimen, and to amplify the specific segment of genomic DNA between the two flanking primers using enzymatic synthesis and temperature cycling. Each pair of primers are designed to hybridize only to the HSV DNA to which they have been synthesized to complement; one to each strand of the double-stranded DNA. The region to which the primers have been synthesized to complement is conserved in HSV; i.e., the primers are generic to HSV and complement both HSV-1 and HSV-2. Thus, the reaction is specific even in the presence of microgram quantities of heterologous DNA.

The enzymatic amplification reaction-liquid hybridization system of the present invention is used for the identification of the amplified DNA fragment, as being derived from HSV DNA. This method utilizes one or more oligonucleotides labeled with detectable moiety as probes to specifically hybridize to the amplified segment of HSV DNA. However, at this stage of the system, the oligonucleotide probes have been synthesized to be specific for either HSV-1 or HSV-2. Thus, in the detection of amplified specific HSV nucleic acid sequences, the system according to the present invention can distinguish between serotypes of HSV; i.e., HSV-1 from HSV-2. Detection of the presence of sequence-specific amplified HSV DNA may be accomplished using a gel retardation assay with subsequent detection of the complex comprising the labeled oligonucleotide hybridized to the sequence-specific amplified HSV DNA.

In such a enzymatic amplification reaction-liquid hybridization system of HSV detection, a clinical specimen of CSF, body secretions, or other body fluid is subjected to a rapid DNA extraction procedure. Then, for example, the DNA extracted from the clinical specimen is enzymatically amplified in the polymerase chain reaction using HSV-specific oligonucleotides (SEQ ID NO:7 & SEQ ID NO:8; or SEQ ID NO:9 & SEQ ID NO:10) as primer pairs. Following amplification, an HSV-specific oligonucleotide (SEQ ID NO:11 or SEQ ID NO: 12, for use with SEQ ID NOs:7 & 8; or SEQ ID NO:13 or SEQ ID NO:14, for use with SEQ ID NOs:9 & 10) radiolabeled with $^{32}P$, or labeled with a detectable moiety, is hybridized to the amplified target sequences, if present.

The contents of the hybridization reaction are then analyzed by electrophoresis on a polyacrylamide gel. If the sequence-specific amplified HSV DNA is present in the DNA extract from the clinical specimen, the migration of the labeled oligonucleotide probe through the gel will be retarded by hybridization with the sequence-specific amplified HSV DNA. Visualization of this gel retardation can be accomplished by autoradiography in 24–48 hours. Alternatively, by labelling the oligonucleotide probe with a fluorescent molecule, or by electrophoresing the amplified DNA in the presence of a fluorescent intercalating dye, the acrylamide gel can be scanned by a fluorescent imager for fluorescent DNA thereby allowing completion of the assay in 6 hours.

Using the oligonucleotides and the enzymatic amplification reaction-liquid hybridization system for HSV detection according to the present invention, and using radiolabeled oligonucleotide probes, 10 to 20 $TCID_{50}$ (tissue culture infective dose, 50%) of HSV DNA has been detected in samples containing 10 micrograms of heterologous DNA. Using the oligonucleotides and the system for HSV detection according to the present invention, and using fluorescent imaging, 0.03 $TCID_{50}$ of HSV DNA has been detected in samples containing 10 micrograms of heterologous DNA. Further, using the system and compositions according to the presently invention, HSV-1 can be successfully distinguished form HSV-2 in clinical specimens. Thus, the oligonucleotides of the present invention have commercial applications in diagnostic kits for the detection of HSV serotype-specific DNA in clinical specimens.

EXAMPLE 1

5.4 DNA Extraction

High molecular weight DNA, including herpesvirus DNA, may be purified from blood cells, tissue cells, or virus particles (collectively referred to herein as "cells") contained in the clinical specimen using proteinase (proteinase K) extraction and ethanol precipitation. The clinical specimen (e.g., 1 ml) was centrifuged to pellet the cells. The pellet of cells was resuspended in a buffer containing 200 μl of 100 mM KCl, 10 mM Tris pH 8.3, and 150 mM $MgCl_2$, in creating a cell suspension. The suspension was then transferred to a cryovial containing 200 μl of 10 mM Tris pH 8.3, 25 mM $MgCl_2$ and detergent (e.g., 1% NP40™ and 1% Tween 20™) to dissolve cell membranes and to inhibit DNases and RNases that may be present. 2.5 μl of 20 mg/ml of Proteinase K was added to digest proteins. The solution was either incubated overnight at 37° C. or at 60° C. for 1 hour. The proteinase K was inactivated at 98° C. for 10 minutes. The DNA extract was mixed with an equal volume of phenol/chloroform/isoamyl alcohol (25:24:1) and centrifuged for 2 minutes at 16,000 xg at 4° C. The upper aqueous layer (20 μl) was transferred to a 1.5 ml microfuge tube, and 8 μl of 5M NaCl (final concentration of 0.2M), and 416 μl of absolute ethanol was added. The mixture was placed at −70° C. for at least one hour for precipitation. The precipitate, containing DNA, was centrifuged in the microfuge tube for 15 minutes at 16,000 xg at 4° C. The ethanol was poured off and excess moisture was removed from the microfuge tube. The DNA pellet was then suspended in water or buffer (e.g., to a volume of 200 μl).

DNA may be extracted from a clinical specimen using other methods known in the art. For example, cells contained in the specimen may be washed in TE buffer and pelleted by centrifugation. The cells then may be resuspended in 100 μof amplification reaction buffer containing detergents and proteinase K. Using the polymerase chain reaction, the resultant sample may be composed of the cells in 10 mM Tris pH 8.3, 50 mM KCl, 1.5 mM $MgCl_2$, 0.01% gelatin, 0.45% NP40™, 0.045% Tween 20™, and 60 μg/ml proteinase K. The sample is incubated in a 55° C. water bath for 1 hour. Following the incubation, the sample is incubated at 95° C. for 10 minutes to heat-inactivate the proteinase K. The sample may then be amplified in accordance with the protocol for the polymerase chain reaction as set forth below.

5.5 Nucleic Acid Amplification Method

The purified herpesvirus DNA may be amplified using the polymerase chain reaction (PCR). If purified DNA from the respective herpesvirus sought to be detected is used as a positive control, a concentration of 10–100 pg is usually sufficient for easy detection. DNA to be amplified is distributed in 0.5 ml microfuge tubes using 30 μl of DNA or adjusting the volume to 30 μl with sterile distilled water. A reaction mixture is prepared in sufficient volume to add 70 μl to each individual reaction tube. Stock reagents for the reaction mixture are mixed in the following proportions for each PCR reaction: 10 μl of 10 X PCR buffer (100 mM Tris pH 8.3, 500 mM KCl, 15 mM $MgCl_2$, 0.1% gelatin) 16 μl of dNTPs (1.25 μM each dATP, dCTP, dGTP, dTTP), 0.2 μM of each positive and negative primer, and 1 unit of Taq polymerase. The total volume is achieved by addition of sterile distilled water. The Taq polymerase is added to the reaction mixture just before use and is gently mixed, not vortexed. The reaction mixture is then added (70 μl/tube) to the tubes containing target DNA to be amplified, and the tubes are gently mixed and briefly centrifuged. An overlay of mineral oil, approximately 2 drops, is added to each tube and then the tubes were placed in the thermal cycler. Thirty to thirty-five cycles are generally sufficient for herpesviral DNA amplification. One cycle consists of 1 minute at 94° C., annealing for 1 minute at 55° C., and primer extension for 2 minutes at 72° C. The first cycle includes a 5 minute incubation at 94° C. to assure complete denaturation.

5.6 Primers for Nucleic Acid Amplification

Primer sequences which specifically hybridize to CMV genes for immediate early antigen (IE), or late antigen (LA), complementary to conserved regions of the CMV genome, and used in DNA amplification, are listed in Table 3. The specificity of the primers was based on a genebank database (Genbank) search for each individual sequence. In each case, primer sequences have been selected arbitrarily for low G-C content and analyzed for self annealing using the appropriate computer programs known to those skilled in the art (See for example, Jaeger et al., 1989, *Proc. Natl. Acad. Sci. U.S.A.* 86:7706–7710). Sequences exhibiting free 3' and 5' ends, which exhibited less than 0.5 Kcal/mol of folding at 55° C., were selected and synthesized on an oligonucleotide synthesizer as phosphoramidites. Primer sequences were purified on oligonucleotide purification cartridges according to the manufacturer's directions. Concentrations were determined spectrometrically at 260 nm assuming 1 OD unit is equivalent to 20 μg single stranded oligonucleotide DNA. In the development of a primer pair for the enzymatic amplification of CMV DNA, other primers were tested. However, those other primers were found to be less efficient in amplification, thereby negatively affecting the sensitivity of the assay, compared to the primers of the present invention.

TABLE 3

| Gene/Primer | Genbank Locus | Gene Loction | Sequence No. | Number of Nucleotides | Fragment Length |
|---|---|---|---|---|---|
| IE+ | HS5MIEG | 2189–2206 | SEQ ID NO: 1 | 38 | |
| IE− | HS5MIEG | 2514–2548 | SEQ ID NO: 2 | 37 | 360 |
| IE/probe | HS5MIEG | 2408–2440 | SEQ ID NO: 5 | 33 | |
| LA+ | HS5PPBC | 2081–2110 | SEQ ID NO: 3 | 30 | |
| LA− | HS5PPBC | 2476–2499 | SEQ ID NO: 4 | 25 | 417 |
| LA/probe | HS5PPBC | 2315–2344 | SEQ ID NO: 6 | 30 | |

Primer sequences which specifically hybridize to HSV genes for polymerase (Pol), or thymidine kinase (TK), complementary to conserved regions of the HSV genome, and used in DNA amplification, are listed in Table 4. The specificity of the primers was based on a genebank database (Genbank) search for each individual sequence. In each case, primer sequences have been selected arbitrarily for low G-C content and analyzed for self annealing. In the development of a primer pair for the enzymatic amplification of HSV DNA, at least 5 other primer pairs were tested. However, those other primers pairs were found to be less efficient in amplification, thereby negatively affecting the sensitivity of the assay, compared to the primer pairs of the present invention.

TABLE 4

| Gene/Primer | Genbank Locus | Gene Location | Sequence No. | Number of Nucleotides | Fragment Length |
|---|---|---|---|---|---|
| Pol+ | HS1POL | 2402–2431 HSV-1 | SEQ ID NO: 7 | 30 | |
| | HS2POL | 2059–2088 HSV-2 | | | |
| Pol− | HS1POL | 2740–2769 HSV-1 | SEQ ID NO: 8 | 30 | 367 |
| | HS2POL | 2409–2438 HSV-2 | | | (HSV-1) |
| Pol/probe-HSV | | 2599–2628 HSV-1 | SEQ ID NO: 11 | 30 | 379 |
| Pol/probe-HSV-2 | | 2268–2297 HSV-2 | SEQ ID NO: 12 | 30 | (HSV-2) |
| TK+ | HSV1TK3KB | 367–389 HSV-1 | SEQ ID NO: 9 | 23 | |
| | HSV2TK | 185–208 HSV-2 | | | |

TABLE 4-continued

| Gene/Primer | Genbank Locus | Gene Location | Sequence No. | Number of Nucleotides | Fragment Length |
|---|---|---|---|---|---|
| TK− | HSV1TK3KB | 763–792 HSV-1 | SEQ ID NO: 10 | 33 | 425 (HSV-1) |
| | HSV2TK | 586–604 HSV-2 | | | |
| TK/probe-HSV-1 | | 616–651 HSV-1 | SEQ ID NO: 13 | 37 | 429 |
| TK/probe-HSV | | 191–229 HSV-2 | SEQ ID NO: 14 | 39 | (HSV-2) |

5.7 Probes for Amplified Nucleic Acid Detection

Probe sequences which specifically hybridize within amplified sequences of CMV genes for the immediate early antigen (IE) using the IE primers, or late antigen (LA) using the LA primers, are listed in Table 3. Probe sequences which specifically hybridize within amplified sequences of the HSV-1 gene for polymerase using the Pol primers, or thymidine kinase (TK) using the TK primers, are listed in Table 4. Probe sequences which specifically hybridize within amplified sequences of the HSV-2 gene for polymerase using the Pol primers, or thymidine kinase (TK) using the TK primers, are listed in Table 4. The specificity of the probe was based on a genebank database (Genbank) search for that sequence. Probe sequences were also selected arbitrarily for low G-C content and analyzed for self annealing. Probe sequences were synthesized trytl-off, and were precipitated by butanol as described by Sawadogo and van Dyke (1991, *Nucleic Acid Research* 19(3):674). Concentrations were determined spectrometrically at 260 nm assuming 1 OD unit is equivalent to 20 μg single stranded oligonucleotide DNA.

For purposes of illustrating, but not limiting, the detection method, the oligonucleotides of the present invention which were used as probes were end-labeled with a radioisotope. Probe sequences, internal to the two primers used for amplification of the gene sequence, were end-labeled using $T_4$ polynucleotide kinase and gamma $^{32}P$ ATP. Twenty pMols of probe DNA in kinase buffer (50 mM Tris, pH 7.6, 10 mM $MgCl_2$, 5 mM dithiothreitol, 0.1 mM spermidine-HCl, 0.1 mM EDTA, pH 8.0) was mixed with 120 μCi of gamma $^{32}P$ ATP and incubated at 37° C. for 1 hour. Labeled probe was separated from unincorporated label on an 8% acrylamide gel run for 1 hour at 200 volts in Tris Borate EDTA (TBE) buffer at room temperature. Labeled probe was first located by exposing the acrylamide gel to x-ray film for three minutes. The resulting autoradiogram was then positioned under the gel, and the band containing the labeled probe was excised from the gel. The gel slice was pulverized in one milliliter of sterile distilled water, and the probe was eluted by shaker incubation overnight at 37° C. The eluted probe was separated from the gel fragments by centrifugation using a chromatography prep column. Radioactivity of the probe was determined, by counting one microliter of the labeled probe on a glass fiber filter, by liquid scintillation.

5.8 Detection of Amplified Nucleic Acid Fragments

To identify hybridization between a detectable moiety-labeled oligonucleotide probe with its respective complementary herepesviral amplified sequences, liquid hybridization and gel retardation was employed. For example, hybridization was performed in a total volume of 50 μl containing a mixture of 20 μl of the product from enzymatic amplification and 30 μl of reaction mixture containing 5' $^{32}$P end-labeled oligonucleotide probe (2.5×10$^5$ cpm) in 0.15M NaCl. The mixture was then incubated at 95°–100° C. for 10 minutes to assure complete denaturation of both DNAs; then the mixture was annealed at 55° C. for one hour. After annealing, any hybridized DNA in the sample was separated from unhybridized probe on a 5% acrylamide gel run in TBE at 200 volts for one hour. The gel was transferred onto filter paper, wrapped in plastic, and autoradiographed overnight. The amplified DNA fragments can then be visualized on the autoradiographs.

To avoid contamination by carryover from enzymatic amplifications, sample preparation and amplification reactions were performed in separate laboratories. In addition, reagents were aliquoted, and only pipette tips containing barriers were used, and all other recommended precautions to avoid contamination were adhered to (See for example, Stanier et al., 1992, supra). Each sample was tested three times in three different experiments.

EXAMPLE 2

5.9 Detection of HSV

Figure 1B:
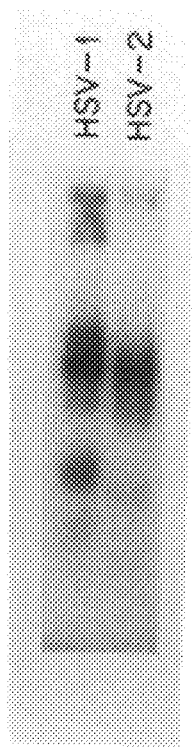
FIG. 1B represents an autoradiogram of enzymatic amplification of HSV-1 genomic DNA and HSV-2 genomic DNA followed by liquid hybridization and gel retardation with an HSV generic polymerase gene probe (SEQ ID NO:11).
Figure 1C:
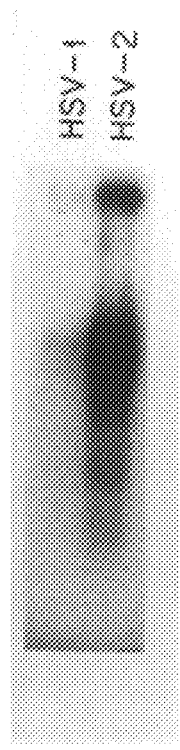
FIG. 1C represents an autoradiogram of enzymatic amplification of HSV-1 genomic DNA and HSV-2 genomic DNA followed by liquid hybridization and gel retardation with an HSV-2 specific polymerase gene probe (SEQ ID NO:12).

This embodiment is in accordance with the procedures and methods described in Example 1. In separate reactions, each of the pairs of primers, illustrated in Table 4, were used to amplify respective specific sequences of the polymerase gene or thymidine kinase gene of HSV. Amplification of the target sequences contained within 1 μg of genomic DNA from each of HSV-1 and HSV-2 was performed by the polymerase chain reaction. The samples amplified also contained 10 mg of DNA from a source other than HSV as a test for specificity of the reaction. Control enzymatic amplification reactions, run in parallel, included a reagent blank (no DNA), and a positive control (containing both HSV-1 and HSV-2 DNA). Liquid hybridization and gel retardation was used to visualize the presence or absence of amplified DNA sequences from the enzymatic amplification reactions of the samples and controls. Using the polymerase gene primers (SEQ ID NOs:7 & 8), the size of the amplified DNA from HSV-1 genomic DNA (FIG. 1A, lane 2) and from HSV-2 genomic DNA (FIG. 1A, lane 3) is consistent with the expected 367 base pair and 379 base pair amplified target sequences, respectively. Autoradiography of a gel containing amplified DNA from HSV-1 genomic DNA (lane 1), and from HSV-2 genomic DNA (lane 2), using the polymerase primers and subsequent liquid hybridization with Pol/probe-HSV generic (SEQ ID NO:11) is represented in FIG. 1B. Note that the Pol/probe HSV generic detects both HSV-1 and HSV-2 amplified DNA. Autoradiography of a gel containing amplified DNA from HSV-1 genomic DNA (lane 1), and from HSV-2 genomic DNA (lane 2), using the polymerase primers and subsequent liquid hybridization with Pol/probe-HSV-2 (SEQ ID NO:12) is represented in FIG. 1C. Note the strong signal in lane 2 containing HSV-2 sequence-specific amplified DNA, and the relative absence of signal in lane 1 containing HSV-1 sequence-specific amplified DNA. Thus, Pol/probe-HSV-2 (SEQ ID NO:12) specifically detects HSV-2 DNA and can be used to distinguish between HSV serotypes, HSV-1 and HSV-2, in a rapid and sensitive assay.

Figure 2A:
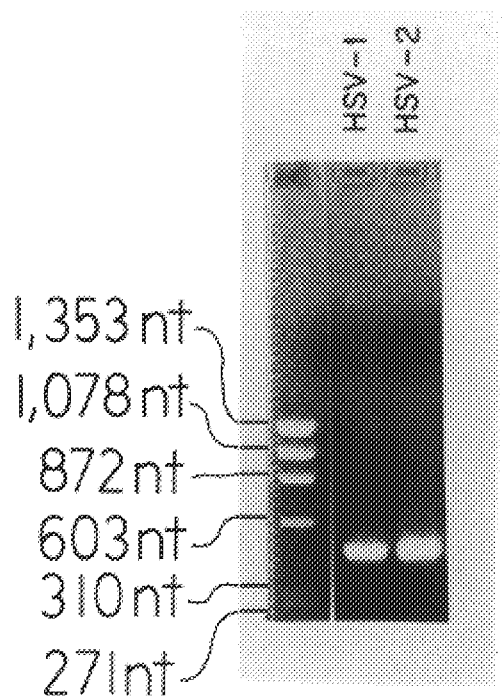
FIG. 2A represents a gel corresponding to enzymatic amplification of HSV-1 genomic DNA and HSV-2 genomic DNA using thymidine kinase gene primers (SEQ ID NOs:9 & 10).
Figure 2B:
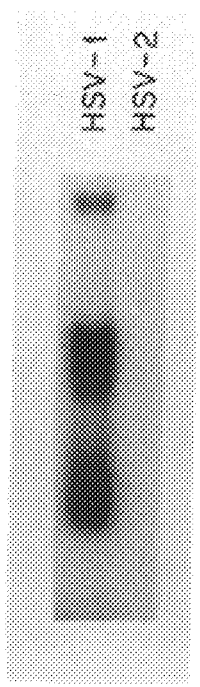
FIG. 2B represents an autoradiogram of enzymatic amplification of HSV-1 genomic DNA and HSV-2 genomic DNA followed by liquid hybridization and gel retardation with an HSV-1 specific thymidine kinase gene probe (SEQ ID NO:13).
Figure 2C:
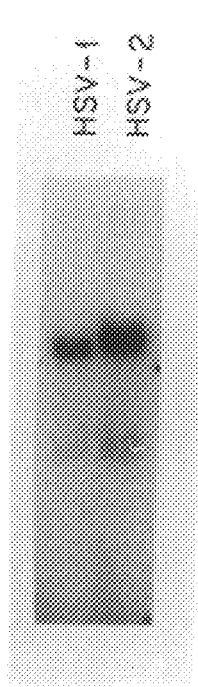
FIG. 2C represents an autoradiogram of enzymatic amplification of HSV-1 genomic DNA and HSV-2 genomic DNA followed by liquid hybridization and gel retardation with an HSV generic thymidine kinase gene probe (SEQ ID NO:14).

Using the thymidine kinase gene primers (SEQ ID NOs:9 & 10), the size of the amplified DNA from HSV-1 genomic DNA (FIG. 2A, lane 2) and from HSV-2 genomic DNA (FIG. 2A, lane 3) is consistent with the expected 425 base pair and 429 base pair amplified target sequences, respectively. Autoradiography of a gel containing amplified DNA from HSV-1 genomic DNA (lane 1), and from HSV-2 genomic DNA (lane 2), using the thymidine kinase primers and subsequent liquid hybridization with TK/probe-HSV-1 (SEQ ID NO:13) is represented in FIG. 2B. Note the strong signal in lane 1 containing HSV-1 sequence-specific amplified DNA, and the relative absence of signal in lane 2 containing HSV-2 sequence-specific amplified DNA. Thus, TK/probe-HSV-1 (SEQ ID NO:13) specifically detects HSV-1 DNA and can be used to distinguish between HSV serotypes, HSV-1 and HSV-2, in a rapid and sensitive assay. Autoradiography of a gel containing amplified DNA from HSV-1 genomic DNA (lane 1), and from HSV-2 genomic DNA (lane 2), using the thymidine kinase primers and subsequent liquid hybridization with TK/probe-HSV generic (SEQ ID NO:14) is represented in FIG. 2C. Note that the TK/probe HSV generic detects both HSV-1 and HSV-2 amplified DNA.

Figure 3:
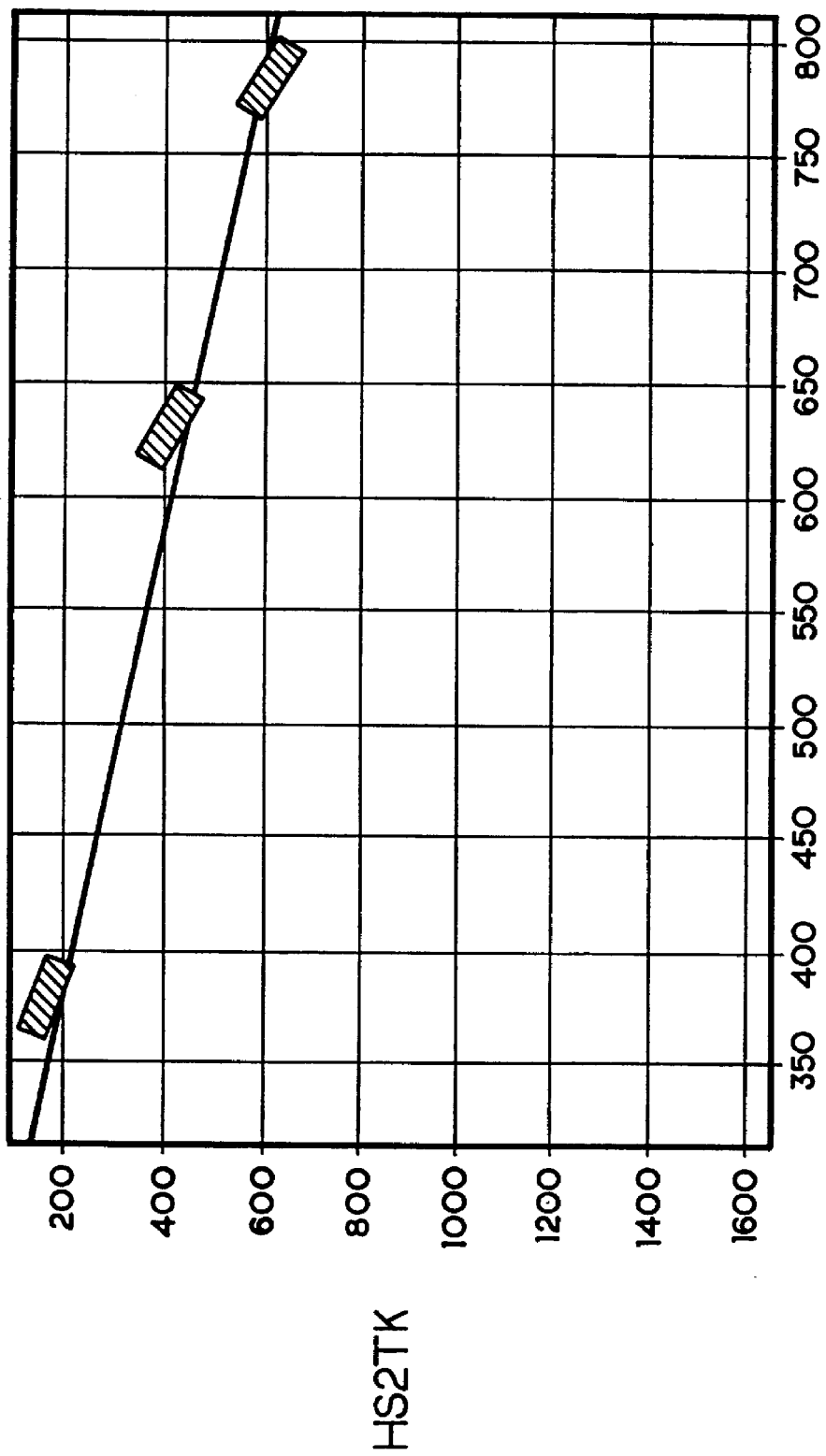
FIG. 3 is a DNA identity matrix plot showing the identity of HSV thymidine kinase primers (SEQ ID NO:9 & SEQ ID NO:10), and TK/probe-HSV-1 (SEQ ID NO:13) relative to HSV-1 and HSV-2 thymidine kinase gene sequences.

FIG. 3 is a DNA identity matrix plot showing the identity of TK+ (SEQ ID NO:9), TK- (SEQ ID NO:10), and TK/probe-HSV-1 (SEQ ID NO:13) relative to HSV-1 and HSV-2 thymidine kinase gene sequences. Similar identity matrix plots for the TK+ (SEQ ID NO:9) and TK- (SEQ ID NO:10) and TK/probe HSV generic; and for Pol+ and Pol- and Pol/probe HSV generic and Pol/probe-HSV-2, were also analyzed and primer sequences were selected from regions of identity in genes of HSV-1 and HSV-2 flanking a region of specificity in each gene from which probe sequences were synthesized.

EXAMPLE 3

6.0 Comparison of Methods to Detect CMV

To illustrate the specificity and sensitivity of the compositions and methods of the present invention for the detection of CMV in clinical samples, 25 patients were monitored for CMV infection using three different assays: the shell vial assay ("SVA"); an antigenemia assay ("AGN"); and an assay according to the present invention (enzyme amplification followed by liquid hybridization and gel retardation ("EA/LH/GR").

One hundred thirteen heparin treated blood samples were obtained from 16 renal transplant patients (Table 5, Nos. 1–16), five HIV-positive patients (Table 5, Nos. 17–21), three patients with non-CMV disease (Table 5, Nos. 22–24) and one patient with CMV pneumonia (Table 5, No. 25). Peripheral blood leukocytes (PBLs) from the blood samples were separated by sedimentation using a 5% dextran solution. Six milliliters of whole blood was mixed with 1.5 ml of 5% dextran solution in phosphate buffered saline (PBS). The blood was incubated at 37° C. for 15–20 minutes at a 45 degree angle until the blood separated into layers. The upper layer containing the PBLs was transferred into a sterile tube and centrifuged for 10 minutes at 300 xg. The contaminating red cells were lysed using 5 ml of a red cell lysing solution (0.826% ammonium chloride, 0.1% potassium bicarbonate, 0.037% EDTA). The leukocytes were washed with 5 ml of PBS, pH 7.4. If red cells were still present, the red cell lysing step was repeated. The remaining cell pellet was suspended in 1 ml of PBS, pH 7.4 and a cell count was performed. PBLs for SVA were suspended at 1×10$^6$ cells/ml in a balanced salt solution. Aliquots for AGN were prepared at 1.5×10$^6$ PBLs/ml in PBS, pH 7.4. PBLs for testing by the method of the present invention (EA/LH/GR) were suspended at 2×10$^6$ cells, and frozen at −70° C. until use.

The SVA was performed by inoculating 1×10$^6$ PBLs/ml into duplicate 1 dram culture vials containing an 11 mm coverslip. The vials were centrifuged at 700 xg for 40 minutes at 37° C., fed with a tissue culture growth medium containing 5% fetal calf serum, and incubated at 36° C. The first vial was fixed and stained on day 2; the second vial was processed on day 5, 6, or 7. Shell vials were stained using a commercial kit for immunofluorescent staining of CMV, according to the manufacturer's instructions. The kit contains a monoclonal antibody that recognizes the immediate early antigen which has been reported to appear in the nucleus as early as 3 hours after infection. At 24 hours post-infection, staining has been observed in the cytoplasm as well as the nucleus.

The CMV AGN was performed by preparing cytospin slides. Briefly, slides were prepared by cytocentrifugation and made to contain approximately 50,000 PBLs. Two slides for each specimen were examined. Most of the PBLs (>95%) will be polymorphonuclear leukocytes (PMNLs). For detection of CMV antigenemia by immunofluorescence, slide preparations were incubated with mouse monoclonal antibodies directed against the CMV lower matrix phosphoprotein. After washing, slides were incubated with goat anti-mouse fluorescein isothiocyanate (FITC) conjugate. Positive cells demonstrated a green nuclear staining when viewed under appropriate magnification using the appropriate microscopy. Results were expressed quantitatively as number of positive cells per 50,000 PBLs.

Figure 4A:
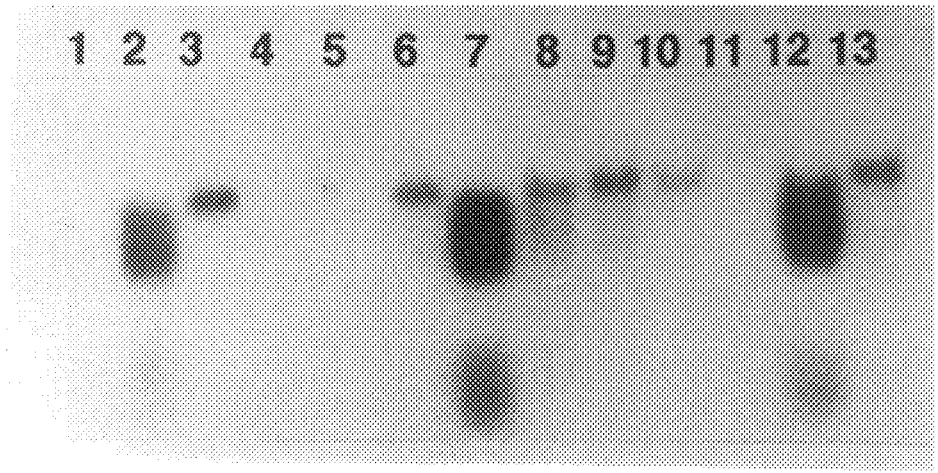
FIG. 4A represents an autoradiogram that illustrates the results obtained from nine patient specimens (lanes 2–10) assayed for the presence of the CMV immediate early gene using the method of the present invention.
Figure 4B:
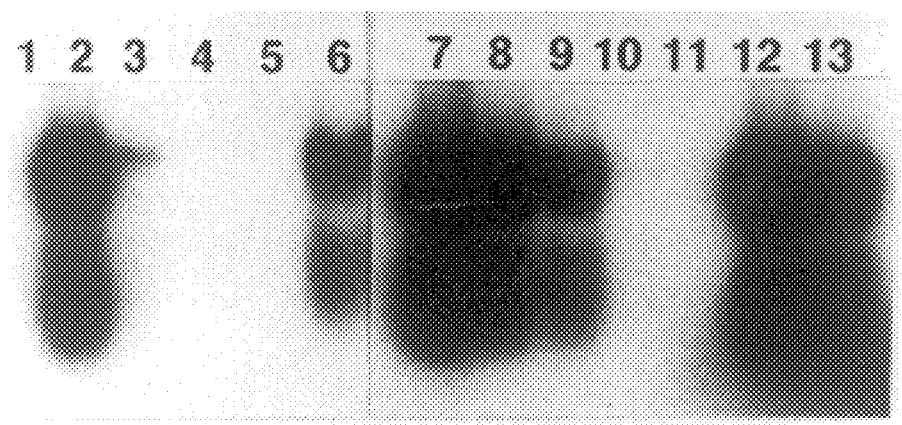
FIG. 4B represents an autoradiogram that illustrates the results obtained from nine patient specimens (lanes 2–10) assayed for the presence of the CMV late antigen gene using the method of the present invention.
Figure 4C:
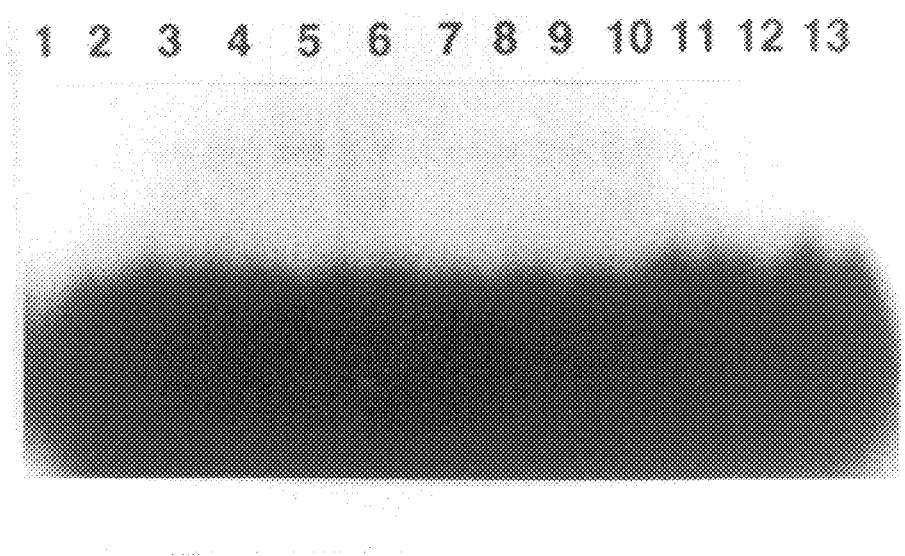
FIG. 4C represents an autoradiogram that illustrates the results obtained from nine patient specimens (lanes 2–10) assayed for the presence of the T cell receptor constant region using the methods according to the present invention.

Detection of CMV using the method of the present invention (EA/LH/GR) was performed in accordance with the procedures and methods described in Example 1. High molecular weight DNA was purified from $2 \times 10^6$ leukocytes, and enzyme amplification with subsequent liquid hybridization and gel retardation was performed. FIGS. 4A, 4B, and 4C illustrate the type of data collected by EA/LH/GR. These figures represent autoradiograms that illustrate the results obtained from nine patient specimens (lanes 2–10) assayed for the presence of the CMV immediate early gene (FIG. 4A) and the CMV late antigen gene (FIG. 4B). In FIGS. 4A & 4B, lane 1 was a reagent control containing no DNA; lane 11 was a negative DNA control; and lanes 12 and 13 were positive controls in which CMV DNA is present at 6 $TCID_{50}$ and 0.6 $TCID_{50}$, respectively.

FIG. 4C shows amplification and detection of T cell receptor (TCR) constant gene region in extracts prepared from patient specimens. This TCR gene, present in all human cells, provides evidence that the DNA extracted from patient leukocytes was sufficient in quantity and quality that the presence of a specific gene would be detected if that gene were present. Detection of this TCR gene was an internal DNA control for the integrity of each DNA extract. Lanes 12 and 13 shown in FIG. 4C contained purified CMV DNA diluted in human T cell DNA at a concentration of 5 µg/ml.

Patient specimens, as indicated in lanes 2, 3, 6, 7, 8, 9, and 10, produced bands when assayed with primers specific for the immediate early gene (SEQ ID NOs:1 & 2) and the respective probe (SEQ ID NO:5); and the CMV late antigen gene (SEQ ID NOs:3 & 4) and the respective probe (SEQ ID NO:6). The bands observed in these lanes migrated at the same rate as bands observed in positive CMV controls, and the reagent control and negative DNA control showed no evidence of contamination. In addition, the signals obtained from CMV controls exhibited band intensities consistent with the quantity of DNA amplified. Having satisfied all these conditions, the specimens in lanes 2, 3, 6, 7, 8, 9, and 10 were declared positive for CMV, while specimens in lanes 4 and 5 were declared negative for CMV.

Table 5 shows a comparison of the three methods for detection of CMV infection by the number of samples that tested positive for each assay over the total number of specimens tested for each patient. Some patients were tested only once, while others were tested repeatedly. The detection of CMV by the method of the present invention (EA/LH/GR) was much more frequent than by the shell viral assay (SVA) and somewhat more frequent than the antigenemia assay (AGN).

TABLE 5

| PATIENT NUMBER | SVA + TOTAL | AGN + TOTAL | EA/LK/GR+ TOTAL |
|---|---|---|---|
| 1 | 1/6 | 4/6 | 6/6 |
| 2 | 0/3 | 2/3 | 2/3 |
| 3 | 3/8 | 5/8 | 8/8 |
| 4 | 0/5 | 2/5 | 2/5 |
| 5 | 6/13 | 12/13 | 13/13 |
| 6 | 0/7 | 0/7 | 0/7 |
| 7 | 0/10 | 4/10 | 7/10 |
| 8 | 0/3 | 0/3 | 0/3 |
| 9 | 4/8 | 3/8 | 7/8 |
| 10 | 0/2 | 0/2 | 1/2 |
| 11 | 0/5 | 0/5 | 0/5 |
| 12 | 5/11 | 8/11 | 10/11 |
| 13 | 7/14 | 11/14 | 13/14 |
| 14 | 2/5 | 4/5 | 4/5 |
| 15 | 0/3 | 0/3 | 0/3 |
| 16 | 0/1 | 0/1 | 0/1 |
| 17 | 0/1 | 0/1 | 1/1 |
| 18 | 0/1 | 0/1 | 0/1 |
| 20 | 0/1 | 0/1 | 0/1 |
| 21 | 0/1 | 0/1 | 0/1 |
| 22 | 0/1 | 0/1 | 0/1 |
| 23 | 0/1 | 0/1 | 0/1 |
| 24 | 0/1 | 0/1 | 0/1 |
| 25 | 1/1 | 1/1 | 1/1 |

Table 6 illustrates not only the frequency of CMV detection by the method of the present invention (EA/LH/GR abbreviated as EA) in comparison with AGN and SVA, but provides evidence of the temporal significance of the more frequent detection. In many patients, the method of the present invention detects CMV before either of the other assays. In most patients, the method of the present invention was more consistently positive than either SVA or AGN during CMV infections.

TABLE 6

| Patient # | Date | SVA | AGN | EA |
|---|---|---|---|---|
| 1. | (6) | | | |
| | 12-27 | -- | +/- | + |
| | 1-20 | -- | + | + |
| | 3-8 | -- | + | + |
| | 3-14 | + | + | + |
| | 3-28 | -- | + | + |
| | 4-11 | -- | +/- | + |
| 2. | (3) | | | |
| | 2-22 | -- | -- | -- |
| | 3-8 | -- | + | + |
| | 3-15 | -- | + | + |
| 3. | (8) | | | |
| | 12-13 | + | + | + |
| | 12-27 | -- | + | + |
| | 1-11 | -- | -- | + |
| | 1-25 | + | + | + |
| | 2-9 | + | + | + |
| | 3-1 | -- | +/- | + |
| | 3-23 | -- | + | + |
| | 4-13 | -- | +/- | + |
| 4. | (5) | | | |
| | 12-14 | -- | -- | -- |
| | 12-27 | -- | -- | -- |
| | 1-18 | -- | -- | -- |
| | 2-23 | -- | -- | + |
| | 3-1 | -- | -- | + |
| 5. | (13) | | | |
| | 12-27 | -- | + | + |

TABLE 6-continued

| | | | | |
|---|---|---|---|---|
| | 1-10 | + | + | + |
| | 1-20 | + | + | + |
| | 1-24 | -- | + | + |
| | 1-31 | -- | + | + |
| | 2-7 | + | + | + |
| | 2-28 | -- | + | + |
| | 3-7 | -- | + | + |
| | 3-14 | + | + | + |
| | 3-28 | -- | + | + |
| | 4-5 | + | + | + |
| | 4-11 | + | + | + |
| | 4-25 | -- | +/- | + |
| 6. | (7) | | | |
| | 12-13 | -- | -- | -- |
| | 12-27 | -- | -- | -- |
| | 1-10 | -- | -- | -- |
| | 1-24 | -- | -- | -- |
| | 2-7 | -- | -- | -- |
| | 2-23 | -- | -- | -- |
| | 3-21 | -- | -- | -- |
| 7. | (10) | | | |
| | 12-13 | -- | -- | -- |
| | 12-27 | -- | + | + |
| | 1-3 | -- | +/- | + |
| | 1-12 | -- | + | + |
| | 1-26 | -- | + | + |
| | 2-9 | -- | -- | -- |
| | 3-8 | -- | + | + |
| | 3-14 | -- | -- | + |
| | 3-28 | -- | -- | + |
| | 4-27 | -- | -- | -- |
| 8. | (3) | | | |
| | 3-29 | -- | -- | -- |
| | 4-11 | -- | -- | -- |
| | 4-13 | -- | -- | -- |
| 9. | (8) | | | |
| | 12-13 | -- | -- | + |
| | 12-29 | + | + | + |
| | 1-5 | -- | -- | + |
| | 1-11 | + | + | + |
| | 1-20 | + | + | + |
| | 2-15 | -- | -- | -- |
| | 3-2 | -- | -- | + |
| | 4-6 | + | -- | + |
| 10. | (2) | | | |
| | 12-27 | -- | -- | -- |
| | 2-22 | -- | -- | + |
| 11. | (5) | | | |
| | 1-25 | -- | -- | -- |
| | 2-7 | -- | -- | -- |
| | 3-23 | -- | -- | -- |
| | 4-5 | -- | -- | -- |
| | 4-26 | -- | -- | -- |
| 12. | (11) | | | |
| | 2-8 | -- | -- | -- |
| | 3-8 | -- | -- | + |
| | 3-17 | + | + | + |
| | 3-23 | + | + | + |
| | 3-28 | -- | + | + |
| | 3-30 | -- | + | + |
| | 4-4 | + | + | + |
| | 4-6 | -- | + | + |
| | 4-13 | -- | + | + |
| | 4-25 | + | + | + |
| | 4-27 | + | +/- | + |
| 13. | (14) | | | |
| | 2-7 | -- | -- | -- |
| | 2-23 | -- | -- | + |
| | 2-28 | -- | -- | + |
| | 3-14 | + | + | + |
| | 3-16 | + | + | + |
| | 3-23 | -- | + | + |
| | 3-28 | -- | + | + |
| | 3-30 | -- | + | + |
| | 4-4 | -- | + | + |
| | 4-6 | + | + | + |
| | 4-11 | + | + | + |
| | 4-13 | + | + | + |
| | 4-15 | + | + | + |
| | 4-25 | + | + | + |
| 14. | (5) | | | |
| | 2-8 | -- | -- | -- |
| | 3-21 | + | + | + |
| | 3-28 | -- | + | + |
| | 4-4 | + | + | + |
| | 4-20 | -- | + | + |
| 15. | (3) | | | |
| | 1-5 | -- | -- | -- |
| | 1-26 | -- | -- | -- |
| | 3-9 | -- | -- | -- |
| 16. | (1) | | | |
| | 1-24 | -- | -- | -- |
| 17. | (1) | | | |
| | 1-24 | -- | -- | -- |
| 18. | (1) | | | |
| | 1-7 | -- | -- | -- |
| 19. | (1) | | | |
| | 1-26 | -- | + | + |
| 20. | (1) | | | |
| | 2-14 | -- | -- | -- |
| 21. | (1) | | | |
| | 2-14 | -- | -- | -- |
| 22. | (1) | | | |
| | 2-15 | -- | -- | -- |
| 23. | (1) | | | |
| | 3-21 | -- | -- | -- |
| 24. | (1) | | | |
| | 4-26 | -- | -- | -- |
| 25. | (1) | | | |
| | 4-26 | + | + | + |

( ) = Numbers in parentheses are number of specimens assayed for each patient
+/- = Only one positive fluorescent cell observed on two slides Patient #1 was tested six times, and all six specimens were positive by the method of the present invention and the antigenemia assay, but only the antigenemia assay detected one infected cell in two of the specimens and SVA was positive in only one of the six specimens. Patient #3 was tested eight times, all of which were positive by the method of the present invention, while seven were positive by AGN wherein two contained only one infected cell, and SVA was only positive in three specimens. Patient #7 was tested ten times, seven of which were positive by the method of the present invention, five were positive by AGN, and none were positive by SVA. Two patients, #4 and #10, provided specimens that were positive only by the method of the present invention. Additional antigenemia slides were assayed (specimen collected 2–22) and a single positive cell was detected on the date 2–22 from patient #10. Further, patient #4 was shedding CMV in urine on the same dates as CMV was apparently detected by the method of the present invention. Patient #4 also had a history of CMV infection three months prior to the date of the specimens which were positive only by the method of the present invention.

Samples were only considered positive by the method of the present invention when both sets of primers for the immediate early gene (SEQ ID NOs:1 & 2) and late antigen (SEQ ID NOs:3 & 4) produced their respective amplified fragments (See FIG. 3). Samples producing a detectable signal with only one primer set were considered negative. By this criteria, samples which were negative by the method of the present invention were also negative by the shell vial assay and the antigenemia assay. No sample positive by the shell vial assay or the antigenemia assay was negative by the method of the present invention. Similarly, unrelated non CMV patients were negative by all three assays, as were four of the renal transplant patients (Nos. 6, 8, 11, and 15). Analysis of the dates of sample collection and the results of the three methods of detection reveal that the method of the present invention detects CMV earlier than either the shell vial assay or the antigenemia assay (see for example, patients Nos. 9, 12, and 13); and both the method of the present invention and the antigenemia assay detect CMV infection in cases where the shell vial assay is negative (see for example, patients Nos. 2, and 7)

When these data are analyzed for specificity and sensitivity, assuming that the shell vial assay is the gold standard for detecting CMV, the limitations of SVA become apparent (Table 7).

table 7

|  | SVA+ | SVA− |
|---|---|---|
| EA/LH/GR+ | 29 | 48 |
| EA/LH/GR− | 0 | 34 |

Total (+) by SVA = 29 samples
Total (−) by SVA = 84 samples
Sensityvity = 100%; Specificity = 41%

The sensitivity of the method of the present invention is defined as the total positive by the shell vial assay is 100% since no specimen positive by the shell vial assay was negative by the method of the present invention. It is important to note that some of the patients from whom samples were collected, were given antiviral therapy which might interfere with SVA but not AGN or the method of the present invention. The specificity of the method of the present invention, defined as the total specimens negative by both the shell vial assay and the method of the present invention divided by the total number of specimens negative by the shell assay, was only 41% because the method of the present invention detected so many more positive samples than were detected by SVA. However, as noted above, antiviral therapy of the patients may have played a role in negative results by SVA. If the same analysis is made using AGN as the gold standard, the sensitivity of the present method remains 100% but the specificity becomes 73%. Patients Nos. 6, 8, 11, and 15 are important to note as no evidence of CMV infection was detected by any of the three methods of analysis, strongly suggesting that the level of false positive detection by the method of the present invention is low.

Comparison between SVA, AGN, and the method of the present invention indicates that the AGN is approximately twice as sensitive as the SVA (55 total positive samples vs. 29 total positive samples); and the method of the present invention is about two and one-half times as sensitive as the SVA (77 total positive samples vs. 29 total positive samples). In addition, it appears that by using the method of the present invention, CMV can be detected in leukocytes up to two weeks earlier than the SVA or AGN.

EXAMPLE 4
6.1 Alternative Methods For Detection

Alternative methods known in the art may be used to improve the detection of amplified target sequences in accordance with the compositions and methods of the present invention. Methods of detection known in the art, in addition to gel electrophoresis and gel electrophoresis with Southern hybridization and autoradiography, that may be used with the compositions and methods of the present invention include: restriction enzyme digestion with gel electrophoresis; slot-blot hybridization with a labeled oligonucleotide probe; amplification with a radiolabeled primer with gel electrophoresis, Southern hybridization and autoradiography; amplification with a radiolabeled primer with dot blot and autoradiography; amplification with oligonucleotides containing affinity tags (ex. biotin, or one primer incorporating biotin and the other primer with a sequence specific for a DNA binding protein) followed by detection in an affinity-based assay (ex. ELISA); and amplification with oligonucleotides containing fluorophores followed by fluorescence detection.

One embodiment of non-isotopic detection involves incorporating biotin into the oligonucleotide primers of the present invention. The 5'-aminogroup of the primers may be biotinylated with sulfo-NHS-biotin, or biotin may be incorporated directly into the primer by synthesizing the primer in the presence of biotin-labeled dNTPs. The non-isotopic labeled primers are then used in amplifying DNA from a clinical specimen as in accordance with the procedures and methods described in Example 1. The detection for the presence or absence of amplified target sequences may be accomplished by capturing the amplified target sequences using an affinity matrix having avidin bound thereto, followed by incubation with an avidin conjugate containing an enzyme which can be used to visualize the complex with subsequent substrate development. Alternately, the amplified target sequences may be immobilized by hybridization to the respective corresponding probes, wherein the probes have been affixed onto a matrix. Subsequent detection may be accomplished using an avidin conjugate containing an enzyme which can be used to visualize the complex with subsequent substrate development.

EXAMPLE 5
6.2 Diagnostic Kits Utilizing the Compositions and Methods

The compositions and methods according to the present invention can be used in the development of diagnostic test kits for herpesviruses. A diagnostic test kit for detection of HSV according to the compositions and methods of the present invention may include, in separate packaging, a lysing buffer for lysing cells contained in the specimen; at least one oligonucleotide primer pair (SEQ ID NO:7 & SEQ ID NO:8; or SEQ ID NO:9 & SEQ ID NO:10; or both SEQ ID NO:7 & SEQ ID NO:8, and SEQ ID NO:9 & SEQ ID NO:10); enzyme amplification reaction components such as dNTPs, reaction buffer, and/or amplifying enzyme; and at least one oligonucleotide probe labeled with a detectable moiety (SEQ ID NO:11 and/or SEQ ID NO:12 for use with primer pair SEQ ID NO:7 & SEQ ID NO:8; or SEQ ID NO:13 and/or SEQ ID NO:14 for use with primer pair SEQ ID NO:9 & SEQ ID NO:10); or various combinations thereof.

Similarly, a diagnostic test kit for detection of CMV according to the compositions and methods of the present invention may include, in separate packaging a lysing buffer for lysing cells contained in the specimen; at least one oligonucleotide primer pair (SEQ ID NO:1 & SEQ ID NO:2; or SEQ ID NO:3 & SEQ ID NO:4; or both SEQ ID NO:1 & SEQ ID NO:2, and SEQ ID NO:3 & SEQ ID NO:4); enzyme amplification reaction components such as dNTPs, reaction buffer, and/or amplifying enzyme; and at least one oligonucleotide probe labeled with a detectable moiety (SEQ ID NO:5 for use with primer pair SEQ ID NO:1 & SEQ ID NO:2; or SEQ ID NO:6 for use with primer pair SEQ ID NO:3 & SEQ ID NO:4), or various combinations thereof.

It should be understood that while the invention has been described in detail herein, the examples were for illustrative purposes only. Other modifications of the embodiments of the present invention that are obvious to those of ordinary skill in the art of molecular biology, medical diagnostics, and related disciplines are intended to be within the scope of the appended claims.

We claim:

1. A composition for the detection of herpes simplex virus, consisting essentially of at least one purified and isolated oligonucleotide consisting of a nucleic acid sequence which complements and specifically hybridizes to a conserved region of a herpes simplex virus gene selected from the group consisting of polymerase, and thymidine kinase, wherein said sequence is selected from the group consisting of SEQ ID NO:7—AACATCACCC GCACCATCTA CGACGGCCAG,
SEQ ID NO:8—TTGTGGGCCT GGATGATGCT GGGGTACAGG,
SEQ ID NO:9—AGGTCCACTT CGCATATTAA GGT,
SEQ ID NO:10—AAGCCCCCAG CACCTGCCAG TAAGTCATCG GCT,
SEQ ID NO:11-ACGCGAGGAG GGCGGGGGCG AGCGGGAGCC,
SEQ ID NO:12-GGACGGGGAC GAGGACGGGG ACGAGCGCGA,
SEQ ID NO:13-AGCAAGAAGC CACGGAAGTC CGCCTGGAGC AGAAAAT,
SEQ ID NO:14-ACTTCGCATA TTAAGGTGAC GCGCGTGGCC TCGAACAGC, and a nucleotide sequence which differs from SEQ ID NO:7, SEQ ID NO:8, SEQ ID NO:9. SEQ ID NO:10, SEQ ID NO:11, SEQ ID NO:12, SEQ ID NO:13, or SEQ ID NO:14 by a one base change or substitution therein.

2. An isolated and purified oligonucleotide primer pair for enzymatic amplification of herpesvirus DNA, consisting essentially of a pair of nucleic acid sequences which complement and specifically hybridize to a conserved region of a herpesvirus gene selected from the group consisting of polymerase, and thymidine kinase, wherein said pair of nucleic acid sequences is selected from the group consisting of:

(a) SEQ ID NO:7—AACATCACCC GCACCATCTA CGACGGCCAG, and SEQ ID NO:8—TTGTGGGCCT GGATGATGCT GGGGTACAGG; and (b) SEQ ID NO:9—AGGTCCACTT CGCATATTAA GGT, and SEQ ID NO:10—AAGCCCCCAG CACCTGCCAG TAAGTCATCG GCT.

3. A method for detecting the presence or absence of herpes simplex virus, wherein the method comprises the steps of:

(a) lysing the cells in a specimen to release nucleic acid molecules;

(b) contacting the nucleic acid molecules with oligonucleotide primer pair SEQ ID NO:7 and SEQ ID NO:8 under suitable conditions permitting hybridization of the oligonucleotides to the nucleic acid molecules;

(c) enzymatically amplifying a specific region of the nucleic acid molecules comprising target sequences of the herpes simplex virus polymerase gene using oligonucleotides SEQ ID NO:7 and SEQ ID NO:8 as primers;

(d) contacting amplified target sequences from step (c), if present, with an oligonucleotide probe selected from the group consisting of SEQ ID NO:11, or SEQ ID NO:12, labeled with a detectable moiety under suitable conditions permitting liquid hybridization of the labeled oligonucleotide probe to amplified target sequences; and (e) detecting the presence of amplified target sequences by detecting the detectable moiety of the labeled oligonucleotide probe hybridized to amplified target sequences in a gel retardation assay;

wherein the presence of the amplified target sequences hybridized to labeled oligonucleotide probe SEQ ID NO:11 correlates to the presence of herpes simplex virus in the specimen; and wherein the presence of the amplified target sequences hybridized to labeled oligonucleotide probe SEQ ID NO:12 correlates to the presence of herpes simplex virus 2 in the specimen with a sensitivity of detection at least as low as 10 $TCID_{50}$.

4. A method for detecting the presence or absence of herpes simplex virus, wherein the method comprises the steps of:

(a) lysing the cells in a specimen to release nucleic acid molecules;

(b) contacting the nucleic acid molecules with oligonucleotide primer pair SEQ ID NO:9 and SEQ ID NO:10 under suitable conditions permitting hybridization of the oligonucleotides to the nucleic acid molecules;

(c) enzymatically amplifying a specific region of the nucleic acid molecules comprising target sequences of the herpes simplex virus thymidine kinase gene using oligonucleotides SEQ ID NO:9 and SEQ ID NO:10 as primers;

(d) contacting amplified target sequences from step (c), if present, with an oligonucleotide probe selected from the group consisting of SEQ ID NO:13, or SEQ ID NO:14, labeled with a detectable moiety under suitable conditions permitting liquid hybridization of the labeled oligonucleotide probe to amplified target sequences; and (e) detecting the presence of amplified target sequences by detecting the detectable moiety of the labeled oligonucleotide probe hybridized to amplified target sequences in a gel retardation assay;

wherein the presence of the amplified target sequences hybridized to labeled oligonucleotide probe SEQ ID NO:13 correlates to the presence of herpes simplex virus 1 in the specimen; and wherein the presence of the amplified target sequences hybridized to labeled oligonucleotide probe SEQ ID NO:14 correlates to the presence of herpes simplex virus in the specimen with a sensitivity of detection at least as low as 10 $TCID_{50}$.

5. A diagnostic test kit for detection of HSV comprising, in separate packaging:

(a) at least one oligonucleotide primer pair selected from the group consisting of SEQ ID NO:7 & SEQ ID NO:8, SEQ ID NO:9 & SEQ ID NO:10, and both SEQ ID NO:7 & SEQ ID NO:8 and SEQ ID NO:9 & SEQ ID NO:10; and (b) at least one oligonucleotide probe labeled with a detectable moiety selected from the group consisting of SEQ ID NO:11, SEQ ID NO:12, SEQ ID NO:13, and SEQ ID NO:14; wherein SEQ ID NO:11 and SEQ ID NO:12 is for use with primer pair SEQ ID NO:7 & SEQ ID NO:8, and wherein SEQ ID NO:13 and SEQ ID NO:14 is for use with primer pair SEQ ID NO:9 & SEQ ID NO:10.

6. The diagnostic test kit of claim 5, further comprising at least one additional reagent selected from the group consisting of a lysing buffer for lysing cells contained in the specimen; enzyme amplification reaction components dNTPs, reaction buffer, and amplifying enzyme; and a combination thereof.

7. A method for detecting the presence or absence of herpes simplex virus, wherein the method comprises the steps of:

(a) lysing the cells in a specimen to release nucleic acid molecules;

(b) contacting the nucleic acid molecules with oligonucleotide primer pair SEQ ID NO:7 and SEQ ID NO:8 under suitable conditions permitting hybridization of the oligonucleotides to the nucleic acid molecules, wherein at least one of oligonucleotides selected from the oligonucleotide primer pair is labeled with a detectable moiety;

(c) enzymatically amplifying a specific region of the nucleic acid molecules comprising target sequences of the herpes simplex virus polymerase gene using oligonucleotides SEQ ID NO:7 and SEQ ID NO:8 as primers; and (d) electrophoresing any amplified molecules present from step (c) and detecting the presence of amplified target sequences by detecting the detectable moiety in the amplified target sequences, wherein the presence of the amplified target sequences correlates to the presence of herpes simplex virus in the specimen with a sensitivity of detection at least as low as 1 $TCID_{50}$.

8. A method for detecting the presence or absence of herpes simplex virus, wherein the method comprises the steps of:

(a) lysing the cells in a specimen to release nucleic acid molecules;

(b) contacting the nucleic acid molecules with oligonucleotide primer pair SEQ ID NO:9 and SEQ ID NO:10 under suitable conditions permitting hybridization of the oligonucleotides to the nucleic acid molecules, wherein at least one of oligonucleotides selected from the oligonucleotide primer pair is labeled with a detectable moiety;

(c) enzymatically amplifying a specific region of the nucleic acid molecules comprising target sequences of the herpes simplex virus polymerase gene using oligonucleotides SEQ ID NO:9 and SEQ ID NO:10 as primers; and (d) electrophoresing any amplified molecules present from step (c) and detecting the presence of amplified target sequences by detecting the detectable moiety in the amplified target sequences, wherein the presence of the amplified target sequences correlates to the presence of herpes simplex virus in the specimen with a sensitivity of detection at least as low as 1 $TCID_{50}$.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
  ( A ) LENGTH: 38 nucleotides
  ( B ) TYPE: nucleic acid
  ( C ) STRANDEDNESS: single- stranded
  ( D ) TOPOLOGY: linear ( i i ) ORIGINAL SOURCE:
  ( A ) ORGANISM: Cytomegalovirus ( i i i ) FEATURE:
  ( A ) LOCATION: GenBank locus HS5MIEG ( i v ) SEQUENCE DESCRIPTION: SEQ ID NO:1:

ATGAAGTGTA TTGGGCTAAC TATGCAGAGC ATGTATGA 38

( 2 ) INFORMATION FOR SEQ ID NO:2:

( i ) SEQUENCE CHARACTERISTICS:
  ( A ) LENGTH: 37 nucleotides
  ( B ) TYPE: nucleic acid
  ( C ) STRANDEDNESS: single- stranded
  ( D ) TOPOLOGY: linear ( i i ) ORIGINAL SOURCE:
  ( A ) ORGANISM: Cytomegalovirus ( i i i ) FEATURE:
  ( A ) LOCATION: GenBank locus HS5MIEG ( i v ) SEQUENCE DESCRIPTION: SEQ ID NO:2:

TTGTCTCTCT CCTCATCCAA AATCTTAAAT ATTTTCT 37

( 2 ) INFORMATION FOR SEQ ID NO:3:

( i ) SEQUENCE CHARACTERISTICS:
  ( A ) LENGTH: 30 nucleotides
  ( B ) TYPE: nucleic acid
  ( C ) STRANDEDNESS: single- stranded
  ( D ) TOPOLOGY: linear ( i i ) ORIGINAL SOURCE:
  ( A ) ORGANISM: Cytomegalovirus ( i i i ) FEATURE:
  ( A ) LOCATION: GenBank locus HS5PPBC ( i v ) SEQUENCE DESCRIPTION: SEQ ID NO:3:

CACGCAACTT TTGGCCGCCA CACCTGTCAC 30

( 2 ) INFORMATION FOR SEQ ID NO:4:

( i ) SEQUENCE CHARACTERISTICS:
  ( A ) LENGTH: 25 nucleotides
  ( B ) TYPE: nucleic acid
  ( C ) STRANDEDNESS: single- stranded
  ( D ) TOPOLOGY: linear ( i i ) ORIGINAL SOURCE:
  ( A ) ORGANISM: Cytomegalovirus ( i i i ) FEATURE:
  ( A ) LOCATION: GenBank locus HS5PPBC ( i v ) SEQUENCE DESCRIPTION: SEQ ID NO:4:

CACCACGCAG CGGCCCTTGA TGTTT                                                25

( 2 ) INFORMATION FOR SEQ ID NO:5:

( i ) SEQUENCE CHARACTERISTICS:
           ( A ) LENGTH: 33 nucleotides
           ( B ) TYPE: nucleic acid
           ( C ) STRANDEDNESS: single- stranded
           ( D ) TOPOLOGY: linear ( i i ) ORIGINAL SOURCE:
           ( A ) ORGANISM: Cytomegalovirus ( i i i ) FEATURE:
           ( A ) LOCATION: GenBank locus HS5MIEG ( i v ) SEQUENCE DESCRIPTION: SEQ ID NO:5:

ACCAAGAACT CAGCCTTCCC TAAGACCACC AAT                                        33

( 2 ) INFORMATION FOR SEQ ID NO:6:

( i ) SEQUENCE CHARACTERISTICS:
           ( A ) LENGTH: 30 nucleotides
           ( B ) TYPE: nucleic acid
           ( C ) STRANDEDNESS: single- stranded
           ( D ) TOPOLOGY: linear ( i i ) ORIGINAL SOURCE:
           ( A ) ORGANISM: Cytomegalovirus ( i i i ) FEATURE:
           ( A ) LOCATION: GenBank locus HS5PPBC ( i v ) SEQUENCE DESCRIPTION: SEQ ID NO:6:

TAGGTGCTTC GGCTCATCAC CAACGTGGAA                                            30

( 2 ) INFORMATION FOR SEQ ID NO:7:

( i ) SEQUENCE CHARACTERISTICS:
           ( A ) LENGTH: 30 nucleotides
           ( B ) TYPE: nucleic acid
           ( C ) STRANDEDNESS: single- stranded
           ( D ) TOPOLOGY: linear ( i i ) ORIGINAL SOURCE:
           ( A ) ORGANISM: Herpes simplex virus ( i i i ) FEATURE:
           ( A ) LOCATION: GenBank locus HS1POL, and HS2POL ( i v ) SEQUENCE DESCRIPTION: SEQ ID NO:7:

AACATCACCC GCACCATCTA CGACGGCCAG                                            30

( 2 ) INFORMATION FOR SEQ ID NO:8:

( i ) SEQUENCE CHARACTERISTICS:
           ( A ) LENGTH: 30 nucleotides
           ( B ) TYPE: nucleic acid
           ( C ) STRANDEDNESS: single- stranded
           ( D ) TOPOLOGY: linear ( i i ) ORIGINAL SOURCE:
           ( A ) ORGANISM: Herpes simplex virus ( i i i ) FEATURE:
           ( A ) LOCATION: GenBank locus HS1POL, and HS2POL ( i v ) SEQUENCE DESCRIPTION: SEQ ID NO:8:

TTGTGGGCCT GGATGATGCT GGGGTACAGG                                            30

( 2 ) INFORMATION FOR SEQ ID NO:9:

( i ) SEQUENCE CHARACTERISTICS:
        ( A ) LENGTH: 23 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Herpes simplex virus ( i i i ) FEATURE:
        ( A ) LOCATION: GenBank locus HSV1TK3KB, and HSV2TK ( i v ) SEQUENCE DESCRIPTION: SEQ ID NO:9:

AGGTCCACTT CGCATATTAA GGT  23

( 2 ) INFORMATION FOR SEQ ID NO:10:

( i ) SEQUENCE CHARACTERISTICS:
        ( A ) LENGTH: 33 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Herpes simplex virus ( i i i ) FEATURE:
        ( A ) LOCATION: GenBank locus HSV1TK3KB, and HSV2TK ( i v ) SEQUENCE DESCRIPTION: SEQ ID NO:10:

AAGCCCCAG CACCTGCCAG TAAGTCATCG GCT  33

( 2 ) INFORMATION FOR SEQ ID NO:11:

( i ) SEQUENCE CHARACTERISTICS:
        ( A ) LENGTH: 30 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Herpes simplex virus 1

( i i i ) FEATURE:
        ( A ) LOCATION: Polymerase gene sequence bases 2599-2628

( i v ) SEQUENCE DESCRIPTION: SEQ ID NO:11:

ACGCGAGGAG GGCGGGGGCG AGCGGGAGCC  30

( 2 ) INFORMATION FOR SEQ ID NO:12:

( i ) SEQUENCE CHARACTERISTICS:
        ( A ) LENGTH: 30 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Herpes simplex virus 2

( i i i ) FEATURE:
        ( A ) LOCATION: Polymerase gene sequence bases 2268-2297

( i v ) SEQUENCE DESCRIPTION: SEQ ID NO:12:

GGACGGGGAC GAGGACGGGG ACGAGCGCGA  30

( 2 ) INFORMATION FOR SEQ ID NO:13:

( i ) SEQUENCE CHARACTERISTICS:
        ( A ) LENGTH: 37 nucleotides

-continued (B) TYPE: nucleic acid
         (C) STRANDEDNESS: single-stranded
         (D) TOPOLOGY: linear (ii) ORIGINAL SOURCE:
         (A) ORGANISM: Herpes simplex virus 1

(iii) FEATURE:
         (A) LOCATION: Thymidine kinase gene sequence bases 616-651

(iv) SEQUENCE DESCRIPTION: SEQ ID NO:13:

AGCAAGAAGC CACGGAAGTC CGCCTGGAGC AGAAAAT                                    37

(2) INFORMATION FOR SEQ ID NO:14:

(i) SEQUENCE CHARACTERISTICS:
         (A) LENGTH: 39 nucleotides
         (B) TYPE: nucleic acid
         (C) STRANDEDNESS: single-stranded
         (D) TOPOLOGY: linear (ii) ORIGINAL SOURCE:
         (A) ORGANISM: Herpes simplex virus 2

(iii) FEATURE:
         (A) LOCATION: Thymidine kinase gene sequence bases 191-229

(iv) SEQUENCE DESCRIPTION: SEQ ID NO:14:

ACTTCGCATA TTAAGGTGAC GCGCGTGGCC TCGAACAGC                                  39